(12) United States Patent
Hobelsberger (10) Patent No.: US 10,458,949 B2
(45) Date of Patent: Oct. 29, 2019

(54) METHOD FOR MEASURING A STATOR CORE OF AN ELECTRIC MACHINE AND MEASURING DEVICE

(71) Applicant: ALSTOM Technology Ltd, Baden (CH)

(72) Inventor: Maximilian Hobelsberger, Wurenlingen (CH)

(73) Assignee: GENERAL ELECTRIC TECHNOLOGY GMBH, Baden (CH)

( * ) Notice: Subject to any disclaimer, the term of this patent is extended or adjusted under 35 U.S.C. 154(b) by 0 days.

(21) Appl. No.: 15/180,669

(22) Filed: Jun. 13, 2016

(65) Prior Publication Data

US 2016/0370324 A1 Dec. 22, 2016

(30) Foreign Application Priority Data

Jun. 19, 2015 (EP) .................................... 15172883

(51) Int. Cl.
*G01N 27/82* (2006.01)
*H02K 11/25* (2016.01)
*G01R 31/34* (2006.01)

(52) U.S. Cl.
CPC ............. *G01N 27/82* (2013.01); *G01R 31/34* (2013.01); *H02K 11/25* (2016.01)

(58) Field of Classification Search
None
See application file for complete search history.

(56) References Cited

U.S. PATENT DOCUMENTS

| 2,578,679 A | * | 12/1951 | Edwards | H02P 9/26 322/20 |
| 4,430,007 A | * | 2/1984 | Wiget | G04C 3/143 368/157 |
| 4,722,226 A | * | 2/1988 | Edmonds | G01N 29/14 73/593 |
| 4,996,486 A | | 2/1991 | Posedel | |
| 6,791,351 B2 | * | 9/2004 | Fischer | G01R 31/343 324/765.01 |
| 2003/0057961 A1 | | 3/2003 | Hobelsberger et al. | |

(Continued)

FOREIGN PATENT DOCUMENTS

EP 3344558 A2 12/1989
EP 1318411 A2 6/2003

(Continued)

OTHER PUBLICATIONS

Sonny James, Getting to the "Core" of Your Generator Stator Problems, Jan. 10, 2011, file:///C:/Users/dpretlow/Desktop/10_01_2011_James.pdf (Year: 2011).*

(Continued)

*Primary Examiner* — Patrick Assouad
*Assistant Examiner* — Demetrius R Pretlow
(74) *Attorney, Agent, or Firm* — Armstrong Teasdale LLP (57) ABSTRACT

A method for measuring a stator core of an electrical machine includes the steps of winding at least one excitation coil around the stator core, applying a discontinuous voltage to the excitation coil(s) to magnetically excite the stator core, and measuring a quantity of the magnetically excited stator core. Further, a corresponding measuring device is disclosed.

16 Claims, 8 Drawing Sheets

(56) References Cited

U.S. PATENT DOCUMENTS

| | | | |
|---|---|---|---|
| 2004/0070404 A1 | 4/2004 | Lee et al. | |
| 2004/0124833 A1 | 7/2004 | Kliman et al. | |
| 2006/0219921 A1* | 10/2006 | Baca .................. | G01R 31/308 250/338.1 |
| 2008/0036336 A1* | 2/2008 | Salem .................. | H02K 11/20 310/68 B |
| 2008/0073984 A1* | 3/2008 | Down .................. | H02K 9/19 310/53 |
| 2009/0179663 A1* | 7/2009 | Hobelsberger ....... | G01R 31/343 324/765.01 |
| 2010/0066315 A1* | 3/2010 | Diatzikis .............. | H02K 11/20 322/99 |
| 2010/0211334 A1* | 8/2010 | Sheikman ............ | G01M 5/0041 702/56 |
| 2010/0295491 A1* | 11/2010 | Schulz ................. | G01R 31/346 318/490 |
| 2010/0320194 A1* | 12/2010 | Koide .................. | H02K 15/12 219/635 |
| 2011/0012637 A1 | 1/2011 | Hobelsberger | |
| 2012/0206162 A1 | 8/2012 | Leonov | |
| 2013/0047748 A1* | 2/2013 | Visintin ............... | G01M 7/00 73/862.381 |
| 2014/0049285 A1* | 2/2014 | Rodriguez ........... | G01H 1/003 324/765.01 |
| 2015/0073733 A1* | 3/2015 | Agapiou .............. | G01R 31/003 702/58 |
| 2016/0020677 A1* | 1/2016 | Sauer .................. | H02K 5/1675 310/68 B |
| 2016/0282173 A1* | 9/2016 | Arend .................. | G01H 1/003 |
| 2017/0126161 A1* | 5/2017 | Hijikata .............. | H02P 21/24 |

FOREIGN PATENT DOCUMENTS

| | | | |
|---|---|---|---|
| EP | 2541751 | A2 | 1/2013 |
| EP | 2806544 | A1 | 11/2014 |
| WO | 200210737 | A2 | 2/2002 |
| WO | 2014094029 | A1 | 6/2014 |

OTHER PUBLICATIONS

Sutton, "Theory of electromagentic testing of laminated stator cores", Insight—Non-Destructive Testing and Condition Monitoring, British Institute of Non-Destructive, Testing, vol. No. 36, Issue No. 4, pp. 246-251, Apr. 1, 1999.

Dosedel, "Inspection of Stator Cores in Large Machines with a Low Yoke Induction Method—Measurement and Analysis of Interlamination Short-Circuits", IEEE Transactions on Energy Conversion, vol. No. 16, Issue No. 1, pp. 81-86, Mar. 2001.

Ramirez-Nino et al., "Novel method for detecting interlamination short-circuits in a stator core based on measurement of eddy-current losses in power generators", Measurement Science and Technology, vol. No. 14, Issue No. 12, pp. 2104-2110, Dec. 1, 2003.

Finley et al., "To Test or Not to Test?—Understanding Electrical and Mechanical Tests performed on Induction Motors," IEEE Industry Applications Magazine, IEEE Service Center, vol. No. 10, Issue No. 5, pp. 22-33, Sep. 1, 2004.

Romary et al., "Real Scale Experimental Devices for Stator Core Fault Analysis", Diagnostics for Electric Machines, Power Electronics & Drives (SDEMPED), IEEE International Symposium on, pp. 71-76, Sep. 5, 2011.

Bertenshaw et al., "Detection of stator core faults in large electrical machines", IET Electric Power Applications, vol. No. 6, Issue No. 6, pp. 295-301, Jul. 5, 2012.

Romary et al., "Offline and Online Methods for Stator Core Fault Detection in Large Generators", IEEE Transactions on Industrial Electronics, IEEE Service Center, vol. No. 60, Issue No. 9, pp. 4084-4092, Sep. 1, 2013.

European Search Report and Written Opinion issued in connection with corresponding EP Application No. 15172883.9-560 dated Dec. 9, 2015.

* cited by examiner

METHOD FOR MEASURING A STATOR CORE OF AN ELECTRIC MACHINE AND MEASURING DEVICE

CROSS-REFERENCE TO RELATED APPLICATION

The present application claims foreign priority benefit under 35 U.S.C. § 119 to commonly-owned EP Patent Application No. 15172883.9 filed 19 Jun. 2015, which is hereby incorporated by reference in its entirety.

TECHNICAL FIELD

Embodiments of the invention relate to a method for measuring a laminated stator core of electrical machines, in particular of large generators in maintenance. Embodiments of the invention relate in particular to improving a device and a method in which the laminated stator core is subjected to an externally applied field current. Commonly, the rotor of the electric machine is removed during the measurements.

BACKGROUND

Large generators and motors are routinely examined for laminate shorts and stability when stationary. Various methods are available for this purpose.

One of the methods to determine laminate shorts comprises the magnetization of the entire laminated body by means of an auxiliary coil at the mains frequency, and the measurement of stray fields on the inner surface of the stator bore. The magnetization is carried out to relatively low values of the magnetic induction, typically to about 10% of the normal operating induction. This method of measurement is also known by the name "low-induction laminate short measurement" or by the name "ELCID" (electromagnetic core imperfection detector).

By way of example, U.S. Pat. No. 4,996,486 describes one method of this type. The prior art is therefore for the laminated stator core to be magnetized by means of an auxiliary coil and a sinusoidal auxiliary voltage applied thereto at the mains frequency, to about one tenth of the operating induction. This auxiliary voltage is normally derived directly from the mains voltage. An electrical recording coil is then moved away from the surface of the stator bore, with the recording coil being located close to the surface of the laminated core.

The currents which flow as a result of the interlaminar short circuits in the laminated core now induce voltages with a characteristic phase angle and amplitude magnitude in the recording coil. The characteristic phase angles and amplitudes make it possible to distinguish between points where there are laminate-short currents and points where there are no laminate-short currents. It is therefore possible to locate laminate shorts, and to assess the magnitude of the short-circuit currents, by means of this stray-field recording coil.

The invention provides alternative solutions to determine laminate shorts and the stability of a stator core.

SUMMARY

Embodiments of the present invention relate to a measuring device and a measuring method. For example, in one embodiment a method for measuring a stator core of an electrical machine includes winding at least one excitation coil around the stator core, applying a discontinuous voltage to the excitation coil(s) to magnetically excite the stator core, and measuring a quantity of the magnetically excited stator core.

BRIEF DESCRIPTION OF THE DRAWINGS

The invention will be explained in more detail in the following text with reference to exemplary embodiments and in conjunction with the drawings, in which.

DETAILED DESCRIPTION

Figure 1:
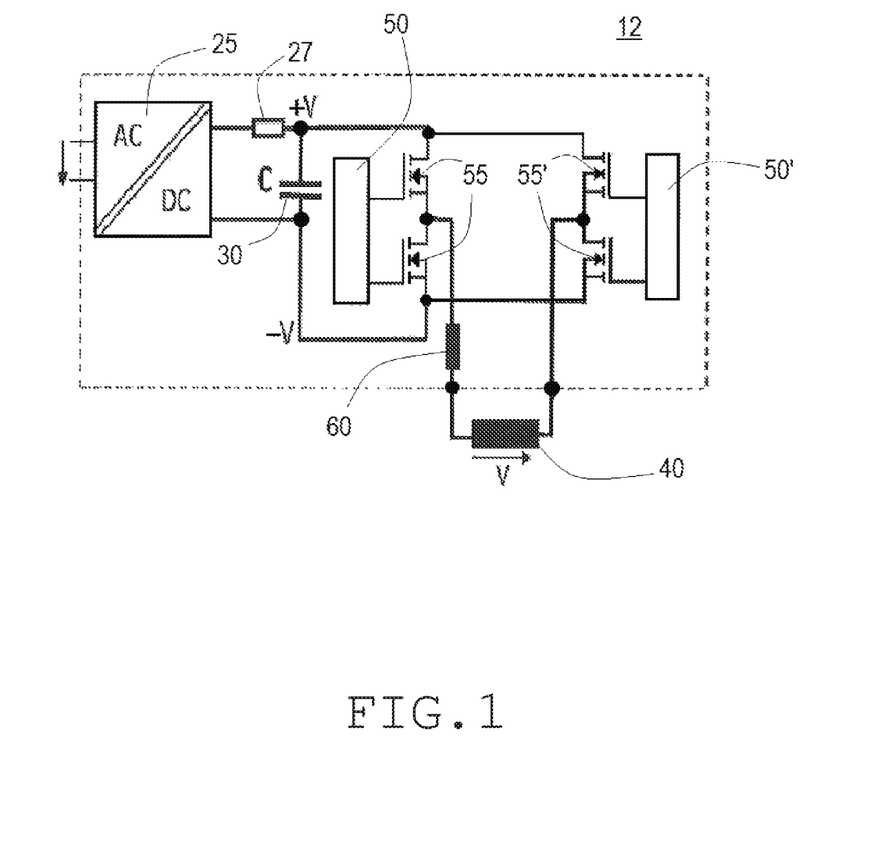
FIG. 1 shows a schematic circuit diagram of an example of an excitation device with one power supply, a resistor and a capacitor operated in parallel, to supply energy to an excitation coil via a circuit comprising IGFETS with controllers, and a filter.

FIG. 1 shows a schematic circuit diagram of an example of an excitation device 12 as part of a measuring device 1 according to an example of the invention. At the left of FIG. 1 a power supply 25 is provided which provides the electric power necessary to charge an excitation coil 40. The power supply 25 can be fed by the public grid. The charging voltage is between 50V and 1000V. The charging voltage is adjusted at the power supply 25 to reach typically 50%-100% of the nominal interlaminar voltage. The maximum permanent power of the power supply 25 is typically 50 kW. The power supply 25 is electrically connected via a resistor 27 and a capacitor 30 to the circuit between the power supply 25 and the excitation coil 40 as shown. The capacitor 30 with a high capacity is charged by the power supply 25 and de-charged via a filter 60 to charge the excitation coil 40 in a specific way. A typical value of the capacitor 30 is 1 mF, a typical value for the excitation coil 40 is 1 mH. The filter 60 is commonly an inductivity which is saturated during current rise. During charge of the capacitor 30 the power supply 25 operates as a current source limiting the current output, during de-charge of the capacitor 30 the power supply 25 operates as a voltage source. In the example according to FIG. 1 the capacitor 30 is connected in parallel with a circuit containing four IGFETs 55, where each two of the IGFETs 55 are steered by a controller 50, 50'. The voltage for the excitation coil 40 is tapped from the circuit containing the IGFETs 55 and the assigned controller 50, 50'. The voltage at the excitation coil 40 can properly be controlled by these means.

Figure 2:
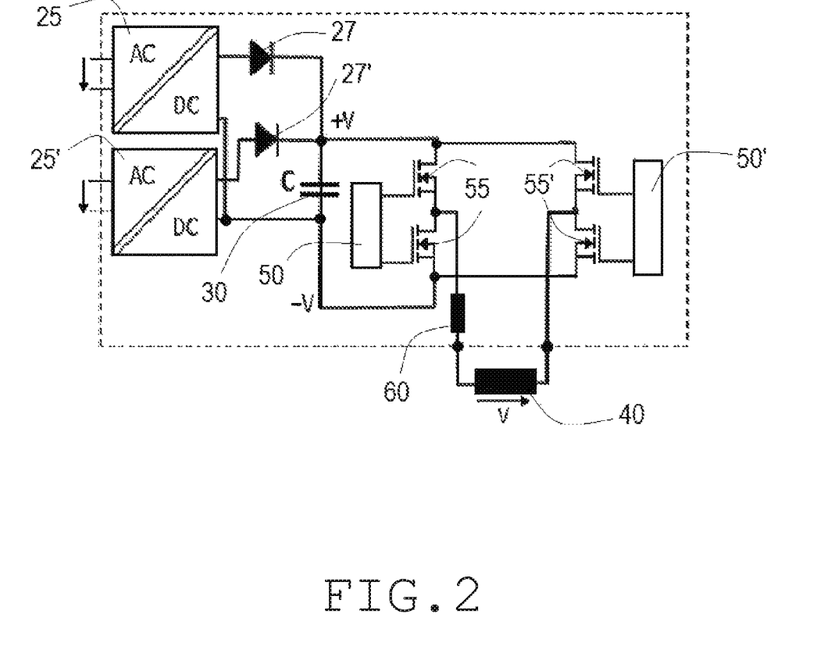
FIG. 2 shows a schematic circuit diagram of an example of an excitation device similar to FIG. 1 with two power supplies connected via diodes.

FIG. 2 shows a schematic circuit diagram of an example of an excitation device 12 similar to FIG. 1 as part of the measuring device 1. Here, the main part of the circuit at the right is identical to the circuit of FIG. 1. The capacitor 30 however is fed by two power supplies 25, 25' instead of one. The two power supplies 25, 25' are connected via diodes 27, 27' in parallel to the capacitor 30. The power output is enhanced compared to the example of FIG. 1 as the second power supply 25' adds additional power to the capacitor 30. The maximum pulse frequency is in this example according to FIG. 2 doubled compared to the example of FIG. 1. An arrangement adding further power supplies 25, 25' to the excitation device 12 is conceivable.

Figure 3:
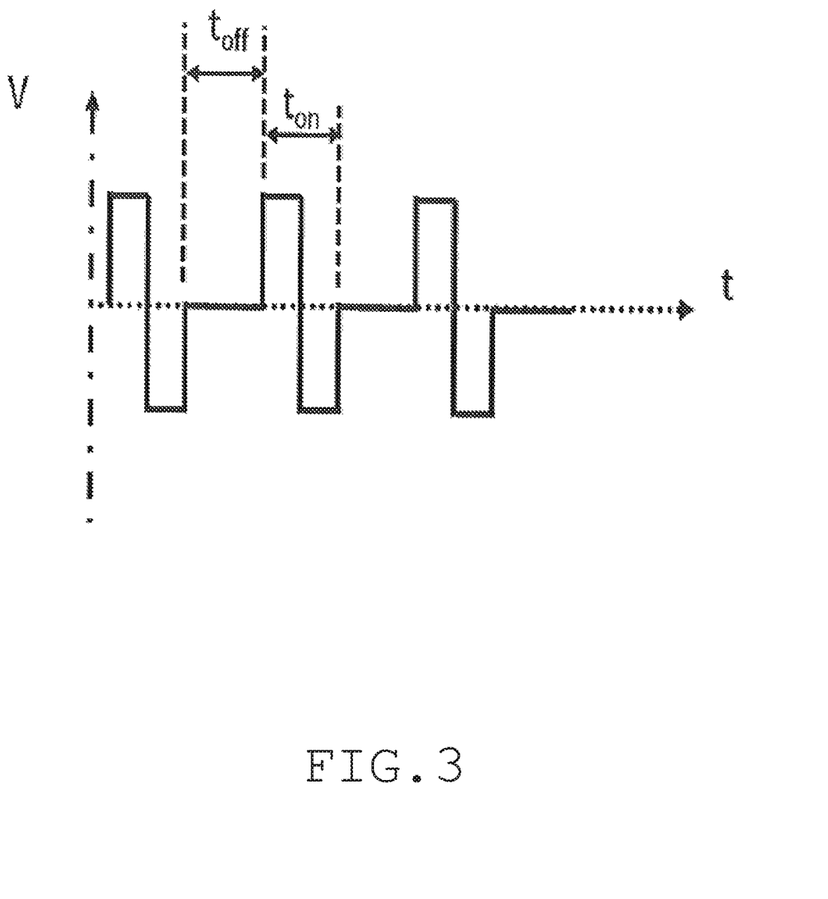
FIG. 3 shows a signal diagram of one example of excitation of a stator core provided by the excitation device to a stator core as a discontinuous voltage with rectangular shape, with the time plotted at the horizontal axis and the voltage plotted at the vertical axis.

FIG. 3 shows a signal diagram of one example of excitation of a stator core 4. The time is plotted at the horizontal axis and the voltage V is plotted at the vertical axis. The signal shown is the voltage generated by the excitation devices 12 to excite the excitation coil 40 as described above. The power supply 25, 25' charges the capacitor 30 which is de-charged in a controlled manner by the controllers 50, 50' switching the IGFETs 55 of the excitation device 12. The shown excitation voltage is applied to the excitation coil 40. As can be seen in FIG. 3 the voltage signal is discontinuous, the times t a voltage is applied are different to the times t the voltage is zero. Here, during the time $t_{ON}$ an excitation voltage is applied consisting of two opposite rectangular pulses, one positive pulse followed by one negative pulse. A typical pulse time is 2 ms-5 ms with 50-100 pulses per second. During the time $t_{OFF}$ the controllers 50, 50' switch the IGFETs to apply no voltage to the excitation device 12. The time $t_{ON}$ is unequal to the time $t_{OFF}$. The control of the excitation device 12 in the way described ensures a low real power and a low reactive power from the feeding grid while assuring high voltages to excite the stator core 4. In the signal shown it equals $t_{ON} < t_{OFF}$.

Figure 4:
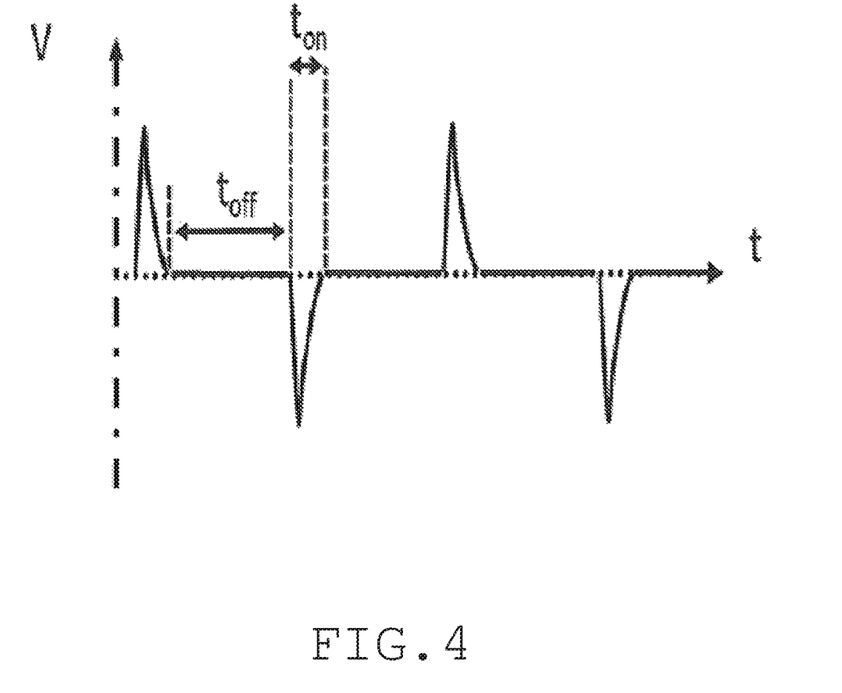
FIG. 4 shows a signal diagram of another example of excitation of a stator core provided by the excitation device to a stator core as a discontinuous voltage with burst shapes, with the time plotted at the horizontal axis and the voltage plotted at the vertical axis.

FIG. 4 shows a signal diagram of another example of excitation of a stator core 4 provided by the excitation device 12 as described above. The time t is plotted at the horizontal axis and the voltage V is plotted at the vertical axis. In this example the voltage signal is discontinuous again. The signal shape of the voltage applied to the excitation coil 40 is the shape of bursts as shown in FIG. 4. First, a steep nearly vertical edge is applied to a maximum power peak which immediately after reaching the peak decays in a steep curve to zero voltage. The time t with a voltage unequal to zero characterized by the voltage burst is referred to as $t_{ON}$. A typical pulse time is 2 ms-5 ms with 50-100 pulses per second. During the time $t_{OFF}$ the controllers 50, 50' switch the IGFETs to apply no voltage to the excitation device 12. The time $t_{ON}$ is unequal to the time $t_{OFF}$. In the signal shown it equals $t_{ON} < t_{OFF}$.

Figure 5:
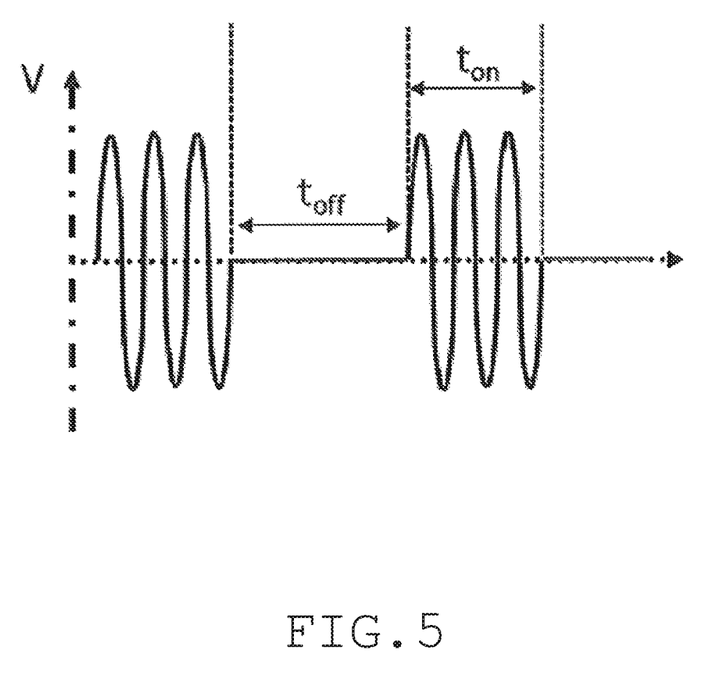
FIG. 5 shows a signal diagram of another example of excitation of a stator core provided by the excitation device to a stator core as a discontinuous voltage with sinusoid shape, with the time plotted at the horizontal axis and the voltage plotted at the vertical axis.

FIG. 5 shows a signal diagram of another example of excitation of a stator core 4 provided by the excitation device 12 with the time t plotted at the horizontal axis and the voltage V plotted at the vertical axis. In this example the stator core 4 is again excited by a discontinuous voltage, here with a sinusoid shape. The time t with a voltage unequal to zero characterized by the sinusoid voltage is referred to as $t_{ON}$. A typical pulse time is 2 ms-5 ms with 50-100 pulses per second. During the time $t_{OFF}$ the controllers 50, 50' switch the IGFETs to apply no voltage to the excitation device 12. The sinusoid voltage is applied with three cycles at the time $t_{ON}$ after which end of the last cycle the excitation voltage is set to zero. In the signal shown it equals $t_{ON} < t_{OFF}$.

Figure 6:
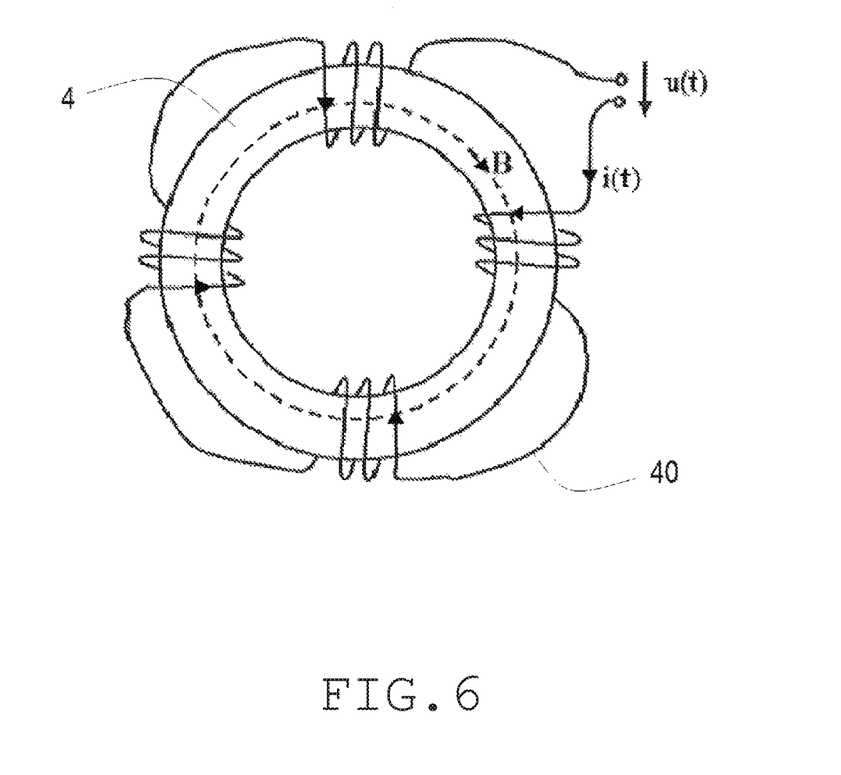
FIG. 6 shows a schematic top view of a stator core to be measured with a schematic excitation coil wound around the stator coil to provide an excitation voltage to the stator core for magnetic excitation of the stator core.

FIG. 6 shows a schematic top view of a stator core 4 of an electric machine. A rotor inside the stator core 4 is removed which is commonly done in measurement mode. In a schematic way the winding of the excitation coil 40 around the stator core 4 is shown which is the excitation coil 40 described under FIG. 1 and FIG. 2. The excitation coil 40 is divided into four connected parts in this example. As described above an excitation voltage u(t) is applied to the excitation coil 40. According to the electro-magnetic theory the current flow i(t) in the excitation coil 40 induces a magnetic flux density B in the stator core 4 in the direction indicated by the arrow. The electric exposure of the stator core 4 is reduced with all three exemplary signal curves with discontinuous voltages. The magnetic flux density B in the stator core 4 is detectable by different measures from which two are described below as two different embodiments of the invention.

Figure 7:
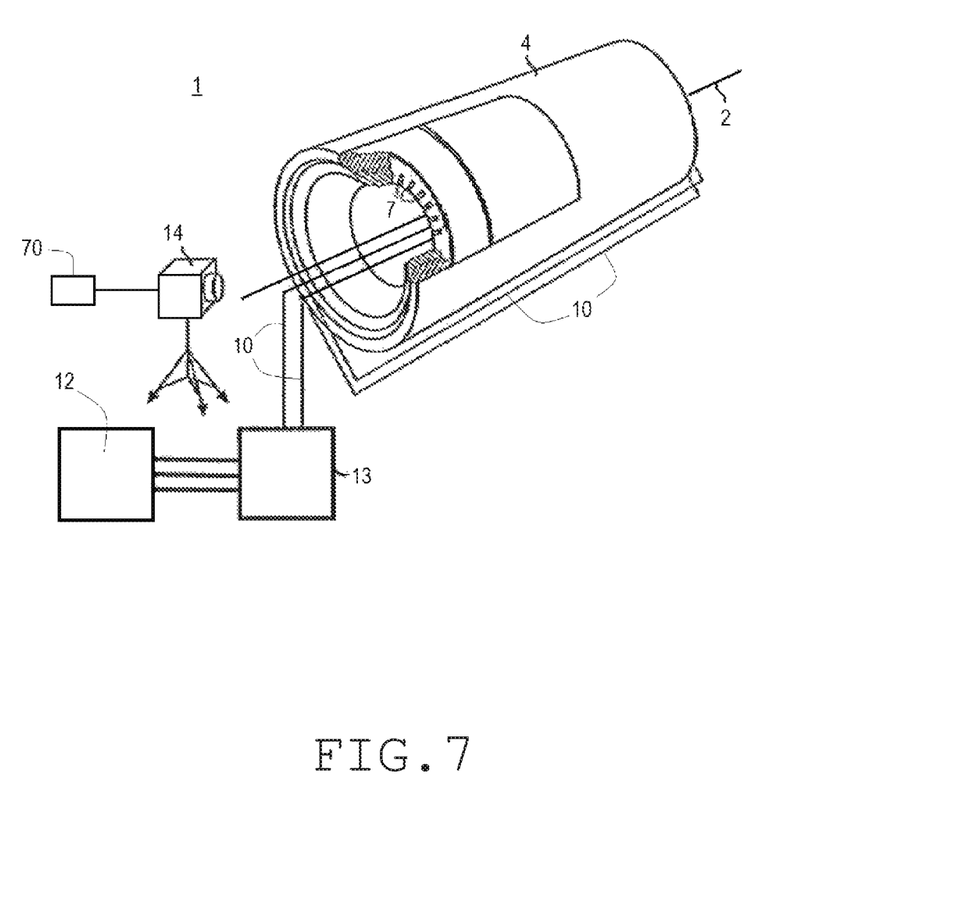
FIG. 7 shows a schematic perspective view of a measuring device with an exciter device connected via a power transformer to excitation windings wound around a stator core and a detection device designed as a camera to optically detect a temperature difference in the vicinity of the stator core.

FIG. 7 shows a first embodiment of the invention. Shown is a schematic perspective view of a measuring device 1 which comprises an excitation device 12 connected via a power transformer 13 to excitation windings 10, 10a, 10b wound around the stator core 4 constituting the excitation coil 40. The stator core 4 is illustrated in a perspective view with partly cut faces and an axis 2. The stator core 4 has a weight of 53 t and a length of 5 m for example. At the inside the stator core 4 commonly has notches 7 to house stator bars (not shown). The excitation coil 40 has ten turns wound around the stator core 4 in this example, shown are only two turns. Switching the excitation voltage by the excitation device 12 and thus magnetizing the stator core 4 leads to a rise in temperature at the surface of the stator core 4. To the end of measuring temperatures and especially temperature differences an optical detection device 14 is provided next to the stator core 4. The quantity to be measured is the temperature in this embodiment. The optical detection device 14 is in this first embodiment an Infrared (IR) camera. The IR camera is suitable to measure the temperatures at the stator core 4 with a high sensitivity. The optical detection device 14 is moved along the surface of the stator core 4 by an operator and records temperature data. The temperature data is compared to stored data such that deviations between the gathered data and stored data can be determined. The detection device 14 comprises a calculation unit 70 and an electronic memory to this end. When the temperature measured at the stator core 4 with magnetic excitation takes an extraordinary high value it can be deduced that at the corresponding spot an interlamination short exists. In particular, when a large temperature difference between specific measured spots occurs the calculation unit 70 identifies an interlamination short at the spot at which the temperature is higher. Interlamination shorts are electric shorts between the insulations of the separate laminated sheets building the stator core 4 impairing the power efficiency of the electric machine and reducing the operation safety. The temperature rise at these spots are mainly caused by undesirable eddy currents flowing there. The temperature rise at these spots was found to have a linear relation to the averaged power brought into the spot.

Figure 8:
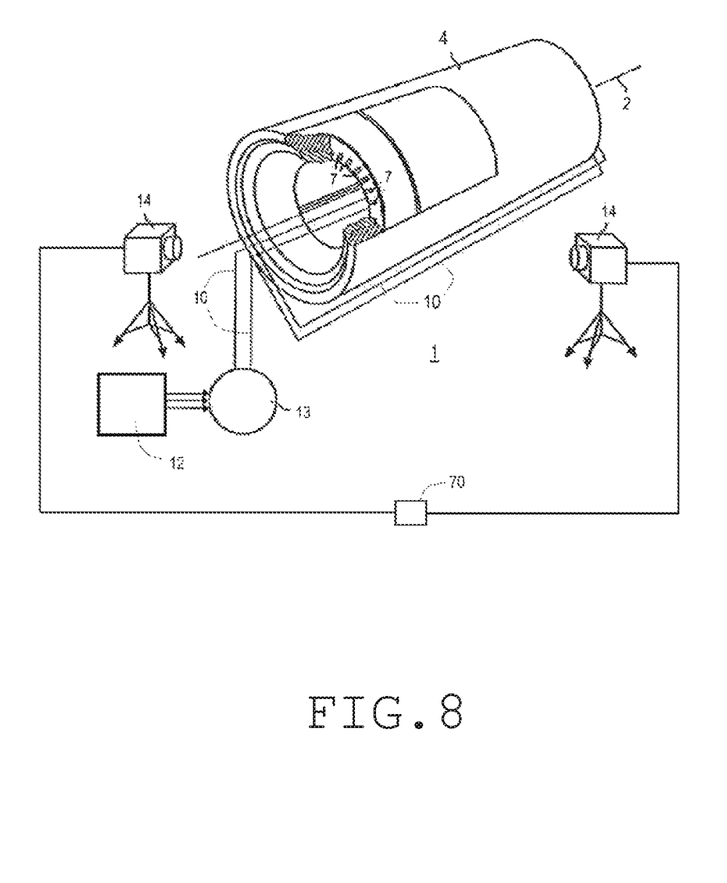
FIG. 8 shows a schematic perspective view of a measuring device with an excitation device connected via a converter to excitation windings wound around a stator core and a detection device designed as two microphones to acoustically detect vibrations in the vicinity of the stator core.

FIG. 8 shows a schematic perspective view of a second embodiment of the invention with a different detection device 14 than the first embodiment. In this embodiment the excitation device 12 is designed the same as in the first embodiment. However, here one typical permanent power is 15 kW. The excitation device 12 is connected to the excitation windings 10 via a converter 13. The excitation windings 10 forming the excitation coil 40 are similar wound around the stator core 4 as in the first embodiment. Here, the windings 10 are arranged in two turns around the stator core 4. The detection device 14 is hereby designed as two microphones, a first microphone or detection device 14 arranged at the left and a second microphone or detection device 14' at the right of the stator core 4. The detection devices 14, 14' can also be designed as vibration sensors. After magnetizing the stator core 4 with discontinuous voltages as described above the microphones are suitable to detect the small vibrations acoustically which are caused by the application of power to the stator core 4. For this purpose the microphones are arranged in close vicinity to the stator core 4 and have a high sensitivity. Generally, this way of detection is based on the fact that the variable magnetic excitation creates vibrations in the whole stator core 4 due to magnetostrictive forces. These vibrations of the stator core 4 are detected by the detection devices 14, 14'. The detection devices 14, 14' are guided along the stator core 4 and measurement results are taken at different spots. The detection devices 14, 14' comprise a calculation unit 70 and an electronic memory. In case of extraordinary values of detected vibrations it can be deduced that a quantity of the stator core 4 diverges at a specific spot. In particular this quantity hereby is the stability of the stator core 4.

What is claimed is:

1. A method for measuring a stator core of an electrical machine comprising:
    winding at least one excitation coil around the stator core;
    applying, via an excitation device comprising at least a capacitor a discontinuous excitation voltage to the at least one excitation coil to magnetically excite the stator core to obtain magnetic excitation of the stator core;
    measuring with at least one detecting device a temperature quantity or a vibration quantity of the magnetically excited stator core; and
    determining interlaminar laminate shorts of the stator core based on extraordinary values of the detected vibration quantity of the magnetically excited stator core measurement, or determining laminated shorts of the stator core based on the temperature quantity of the magnetically excited stator core measurement, the extraordinary values of detected vibrations indicate that a stability of the stator core diverges at a specific spot.

2. The method according to claim 1, wherein the waveform of the discontinuous excitation voltage is rectangular, burst, triangular, or sinusoidal.

3. The method according to claim 2, wherein the discontinuous excitation voltage has pulses of a time duration between 2 ms and 5 ms with a rate between 50 pulses and 100 pulses per second.

4. The method according to claim 3, wherein the excitation device creates the discontinuous excitation voltage with a frequency of 50 Hz or 60 Hz.

5. The method according to claim 4, wherein the excitation device provides the discontinuous excitation voltage to generate a magnetic flux density B of the stator core of approximately 1.5 Tesla.

6. The method according to claim 5, wherein the at least a capacitor provides the discontinuous excitation voltage by discharging.

7. The method according to claim 6, wherein the at least a capacitor is fed by two power supplies coupled together.

8. The method according to claim 7, wherein measuring the quantity of the magnetically excited stator core is by the at least one detecting device, the at least one detecting device comprising an acoustic device measures vibrations of the stator core caused by the magnetic excitation to obtain vibration measurements, and wherein the at least one detecting device or a calculation unit is configured to determine interlaminar laminate shorts of the stator core based on the extraordinary values of detected vibration quantity measurements.

9. The method according to claim 8, wherein the acoustic device comprises at least a microphone.

10. The method according to claim 7, wherein measuring the quantity of the magnetically excited stator core is by the at least one detecting device, the at least one detecting device comprising an optical device measures temperature differences at the stator core caused by the magnetic excitation to obtain temperature measurements, and wherein the at least one detecting device or a calculation unit is configured to determine interlaminar laminate shorts based on the temperature measurements.

11. The method according to claim 10, wherein the discontinuous excitation voltage has pulses of a time duration between 5 ms and 20 ms.

12. The method according to claim 10, wherein the discontinuous excitation voltage has pulses of a time duration between 2 ms and 10 ms.

13. A measuring device for measuring a laminated stator core of an electrical machine comprising:
    at least one excitation coil wound around the stator core;
    an excitation device comprising at least a capacitor for magnetically exciting the stator core to obtain magnetic excitation of the stator core which comprises the at least one excitation coil wound around the stator core, the excitation device configured to generate a discontinuous voltage applicable to the at least one excitation coil to magnetically excite the stator core;
    at least one detection device configured to measure a temperature quantity or a vibration quantity of the magnetically excited stator core to obtain measurements; and
    a calculation unit configured to determine properties of the stator core based on the measurements of the at least one detection device to determine interlaminar laminate shorts of the stator core based on extraordinary values of detected vibration quantity measurements that indicate that a stability of the stator core diverges at a specific spot, or to determine laminated shorts of the stator core based on temperature quantity measurements.

14. The measuring device according to claim 13, wherein the at least one detection device comprises a microphone which measures vibrations of the stator core caused by the magnetic excitation and the calculation unit determines the interlaminar laminate shorts of the stator core via the extraordinary values of detected vibration quantity measurements.

15. The measuring device according to claim 13, wherein the at least one detection device comprises an optical device which measures temperature differences at the stator core caused by the magnetic excitation and the calculation unit determines laminated shorts of the stator core.

16. The measuring device according to claim 13, wherein the at least one detection device comprises an acoustic device which measures vibrations of the stator core caused by magnetic excitation.

* * * * *